United States Patent [19]

Wittry

[11] Patent Number: 4,599,741
[45] Date of Patent: Jul. 8, 1986

[54] SYSTEM FOR LOCAL X-RAY EXCITATION BY MONOCHROMATIC X-RAYS

[75] Inventor: David B. Wittry, Pasadena, Calif.

[73] Assignee: USC—Dept. of Materials Science, Los Angeles, Calif.

[21] Appl. No.: 549,366

[22] Filed: Nov. 4, 1983

[51] Int. Cl.[4] .......................................... G01M 23/00
[52] U.S. Cl. ........................................ 378/85; 378/82; 378/45
[58] Field of Search ...................... 378/85, 84, 83, 82, 378/70, 45, 46, 49, 157.5

[56] References Cited

U.S. PATENT DOCUMENTS

| | | |
|---|---|---|
| 2,688,094 | 8/1954 | Dumond . |
| 2,853,617 | 9/1958 | Berreman . |
| 2,942,126 | 6/1960 | Silbermann ........................ 378/144 |
| 3,229,089 | 1/1966 | Sasao ..................................... 378/85 |
| 3,439,163 | 4/1969 | De Jongh . |
| 3,546,453 | 12/1970 | Browning et al. ..................... 378/85 |
| 3,628,040 | 12/1971 | Schnopper et al. . |
| 3,772,522 | 11/1973 | Hammond et al. . |
| 3,777,156 | 12/1973 | Hammond et al. . |
| 3,898,455 | 8/1975 | Furnas . |
| 3,914,605 | 10/1975 | Hara ...................................... 378/83 |
| 3,920,984 | 11/1975 | Kirkendall et al. .................... 378/83 |
| 3,927,319 | 12/1975 | Wittry . |
| 4,048,496 | 9/1977 | Albert .................................... 378/45 |
| 4,192,994 | 3/1980 | Kastner . |
| 4,203,034 | 5/1980 | Carroll, Jr. . |
| 4,461,017 | 7/1984 | Koga et al. ............................ 378/44 |

OTHER PUBLICATIONS

L. S. Birks, "X-ray Spectrochemical Analysis", Interscience Publishers, 1959.
R. W. James, "The Optical Principles of the Diffraction of X-rays", G. Bell and Sons, 1958.
Gilman, "Plastic Anisotropy of LiF and Other Rocksalt Type Crystals", ACTA Metallurgica, vol. 7, Sep. 1959.
Hagg et al., "Aluminium Monochromator with Double Curvature for High-Intensity X-ray Powder Photographs", Acta. Cryst. (1952) 5, 78.
L. S. Birks, "Electron Probe Microanalysis", Wiley-Interscience, 1971.
Stokes et al., "Environmental Effects on the Mechanical Properties of Ionic Solids with Particular Reference to the Joffe Effect", Trans. of the Metallurgical Society of AIME, vol. 218, Aug. 1960.

Primary Examiner—Craig E. Church
Assistant Examiner—Charles F. Wieland
Attorney, Agent, or Firm—Nilsson, Robbins, Dalgarn, Berliner, Carson & Wurst

[57] ABSTRACT

A system for X-ray fluorescence analysis utilizes a plurality of parfocal diffractors to selectively monochromatize X-rays and focus them on a sample to be analyzed. In a preferred embodiment, each diffractor comprises a toroidally shaped crystal structure which, in the operative position of the diffractor, satisfies Johannson geometric conditions within a plurality of planes containing both a source of X-rays and a focused X-ray image.

18 Claims, 15 Drawing Figures

FIG. 6 METHODS OF DIFFRACTOR FABRICATION

SYSTEM FOR LOCAL X-RAY EXCITATION BY MONOCHROMATIC X-RAYS

BACKGROUND OF THE INVENTION

The present invention relates to the field of X-ray diffraction and, more particularly, to a system for local X-ray excitation by monochromatic X-rays.

Prior chemical analysis techniques include electron probe microanalysis and X-ray fluorescence analysis. In both, X-rays produced by bombardment of a sample are analyzed to determine sample composition. The electron probe can be highly localized on the sample, but produces an undesirably high background noise level. This is primarily due to the presence of bremsstrahlung, along with characteristic lines of the sample. In some cases, the background is equal in magnitude to an output signal representing a sample concentration as high as 0.2% to 1.0%. An electron probe can also destroy radiation sensitive materials, and is not practical for use in analyzing uncoated insulators because of a charging effect.

In chemical analysis with an X-ray probe, collimated X-rays are often obtained by selecting a small segment of a beam. However, this is wasteful of energy, requires a high power X-ray source and does not provide small excitation regions.

The prior systems known to applicant for improved detection limits in X-ray fluorescence analysis rely on polarized radiation or secondary fluorescence radiation. In the former case, X-rays are scattered from a polarizing target and then directed onto a sample to cause fluorescence. Secondary fluorescence systems irradiate samples with independenty produced fluorescence X-rays. However, neither system provides adequate localization of X-rays for microanalysis, i.e., analysis of regions on the order of 100 microns or less in diameter.

A number of prior X-ray monochrometers use diffraction crystals bent in more than one direction. Such doubly curved crystals roughly monochromatize and approximately focus X-rays, as described in the following U.S. patents: Hammond et al, U.S. Pat. No. 3,772,522; Hammond et al, U.S. Pat. No. 3,777,156; Berreman, U.S. Pat. No. 2,853,617; Carroll, Jr., U.S. Pat. No. 4,203,034; and Furnas, U.S. Pat. No. 3,898,455. The crystals do not accurately focus or monochromatize an X-ray beam because they conform to Johann geometry rather than the more accurate Johannson configuration, or are bent in spherical or cylindrical shapes. The Hammond et al '522 patent briefly discusses a crystal geometry which would permit point focusing, but discards it as being too difficult to make. The point focusing geometry is described by Hammond as having the equivalent of Johannson geometry in the plane of a Rowland circle, and being toroidally bent in a perpendicular direction to a radius equal to $D_R \sin^2 \theta$, where $D_R$ is the diameter of the Rowland circle and $\theta$ is the Bragg angle. The Furnas patent also describes a toroidal crystal arrangement, but the crystals are used in the Johann geometry and therefore provide poor monochromatization and poor focusing.

Certain monochrometers and spectrometers have multiple diffraction crystals selectable for use with X-rays of different wavelengths. For example, wavelength dispersive spectrometers (WDS) typically contain multiple diffractors rotatable about an axis for switching between wavelengths. However, such diffractors are typically arranged with the concave surfaces of the crystals facing outwardly from the axis of movement. In these cases the diffractors and image points are also moved relative to the X-ray source and to each other throughout the analysis process. Movement is required when switching from one diffractor to another, and for scanning the wavelength range of the diffractor being used.

The Furnas patent, in the embodiment of FIG. 7 thereof, discloses a toroidal diffraction element made up of three sections focusing X-rays between the same source and image points. However, the sections are used simultaneously and are not selectable to vary the wavelength of focused X-rays. Even if the X-ray paths to two of the sections were blocked for the purpose of selecting a wavelength diffracted by the other, X-rays would impinge upon the target from significantly different directions depending upon the section selected. This difference in direction makes the Furnas device impractical for microanalysis because X-rays of the different wavelengths would encounter imperfections in a sample surface from different directions, causing the results to vary from one wavelength to another.

Therefore, it is desirable in many applications to provide an improved system for X-ray microanalysis which does not require a high power X-ray source and is able to provide a high signal to background ratio from very small regions of a sample.

SUMMARY OF THE INVENTION

In a first aspect, the present invention comprises a selectable X-ray monochrometer comprising: means for defining preselected source and image locations; a plurality of diffracting crystal means selectively actuable to respective operative positions relative to the source and image locations; each diffracting means being constructed and arranged in the operative position thereof to focus X-rays emanating from the source location onto the image location; and the diffracting means being parfocal with each other relative to the source and image locations. In a preferred embodiment, each diffracting means comprises toroidal crystal means which, in the operative position of the diffracting means, satisfies Johannson geometric conditions within a plurality of planes containing the source and image locations. That is, each diffracting means may comprise toroidal crystal means having a plurality of substantially parallel atomic planes adjacent to a primary crystal surface, the crystal surface coinciding with a plurality of Rowland circles of preselected radius which contain the source and image locations in the operative position of the diffracting means, and the atomic planes being curved in the plane of each Rowland circle to twice the Rowland circle radius.

In another embodiment, the monochrometer includes an anode containing a plurality of preselected target materials, and means for selectively bombarding the target materials with an electron beam to generate X-rays of preselected spectra at the source location. The diffracting crystal means are preferably mounted for rotation together about a preselected axis for movement between the respective operative positions, and the preselected axis preferably passes through the source and image locations.

In another aspect, the invention comprises an apparatus for X-ray microanalysis including: means for generating X-rays emanating from a source location over a preselected solid angle; a plurality of diffracting crystal means selectively actuable to respective operative positions relative to the source location and an image location; each diffracting means being constructed and arranged in the operative position thereof to transform the X-rays emanating from the source to X-rays of a respective preselected wavelength, and to focus the X-rays of the preselected wavelength at the image location; the diffracting means having different preselected diffracting properties and being parfocal with each other relative to the source and image locations; means for exposing a sample to the focused X-rays at the image location and means for detecting and analyzing fluorescence X-rays emitted by the sample. In a preferred embodiment, the apparatus comprises optical means for viewing the sample during fluorescence and means for adjusting the area of the sample at which fluorescence occurs.

The use of toroidally shaped diffraction crystals satisfying the Johannson condition, and the parfocal arrangement of those crystals, enables the system of the present invention to provide quantitative analytical information as to the makeup of highly localized areas of a sample. Detection limits are improved significantly over the prior systems, and can be as low as approximately one part per million or less depending on measurement time. The use of three or more diffractors permits the major portion of the periodic table to be covered with more uniform sensitivity.

The invention uses highly monochromatic radiation to eliminate bremsstrahlung, which is responsible for much of the background noise in any X-ray analysis system, and focuses the radiation to an area between 10 and 25 microns in diameter. The diffraction crystals are "parfocal" with each other, as the objective lenses of a microscope are parfocal when they have different powers of magnification but are used at the same working distance. Thus, the crystals accurately focus X-rays between common source and image points. The predominant difference between the crystals is in their diffraction parameters. Each diffraction crystal has its own Rowland circle radius and lattice parameters, defining one wavelength of X-rays which can be reflected with constructive interference (i.e., monochromatized) and focused, for a given order of diffraction.

The toroidal diffraction crystal of the present invention satisfies Johannson geometric constraints within a set of planes containing both the source and image point of the system. The surface is defined by rotating a planar Johannson curve through a preselected angle about the line joining the source and image points. Thus, all radiation within a given solid angle from the source impinges on the crystal in a manner which satisfies Bragg's law, monochromatizing the radiation by constructive reinforcement and focusing the radiation at the image point. Under Bragg's law, radiation of a particular wavelength scattered from parallel layers of atoms of a crystal undergoes constructive interference at predetermined angles of incidence. This phenomenon is responsible for producing monochromatic radiation, and the shape of the crystal is responsible for focusing the radiation to a point.

The considerations discussed above combine to monochromatize and focus a large solid angle of X-radiation, making it possible to detect very small traces of elements at localized areas of a sample. The parfocal diffraction elements permit excitation of a broad enough range of fluorescence-excited radiation to analyze a large portion of the periodic table. Selectable anode targets, an optical viewing system and a sample positioning apparatus, combine with these features to provide a highly versatile and sensitive system.

DESCRIPTION OF THE PREFERRED EMBODIMENTS

Figure 1:
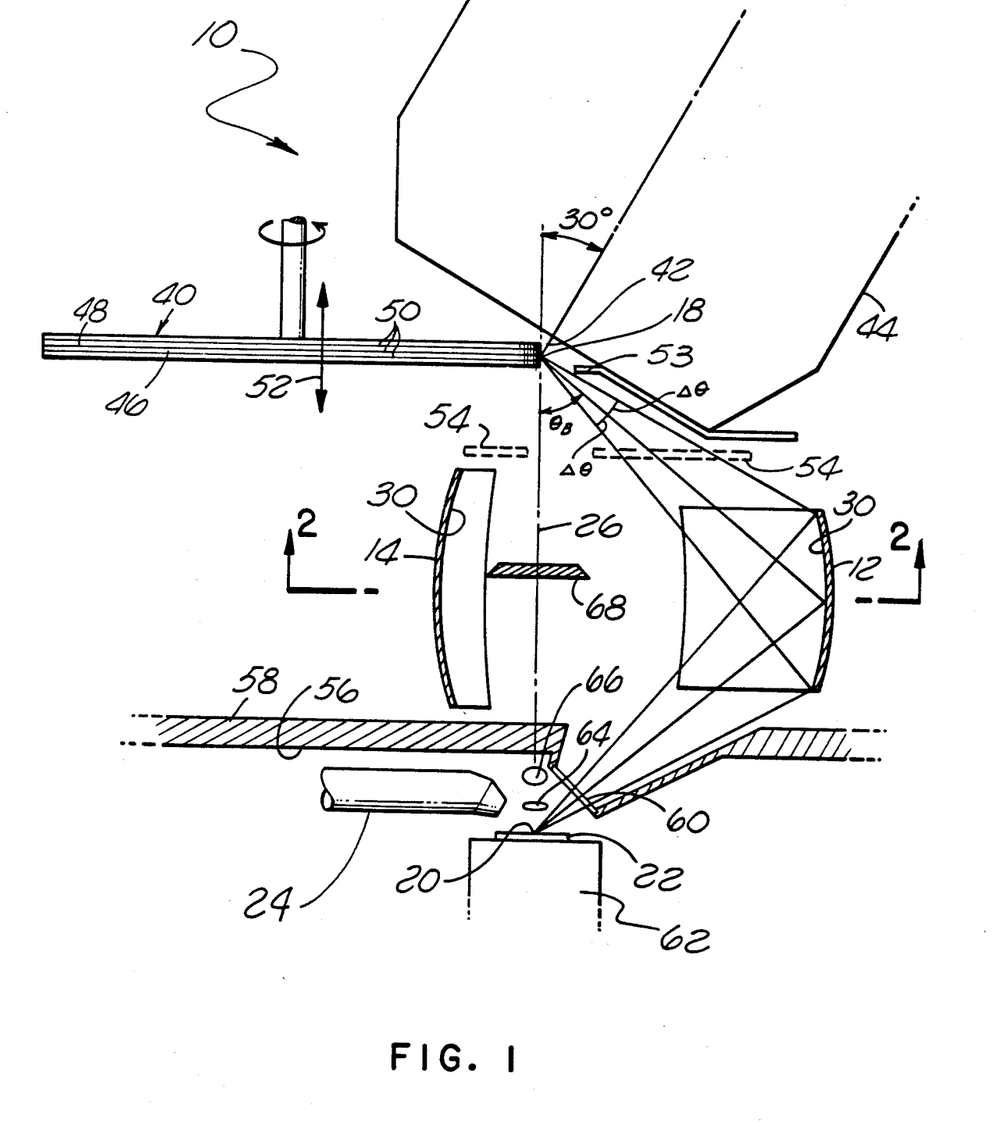
FIG. 1 is a somewhat diagrammatic representation of a fluorescence microanalysis system constructed according to a preferred embodiment of the invention.
Figure 2:
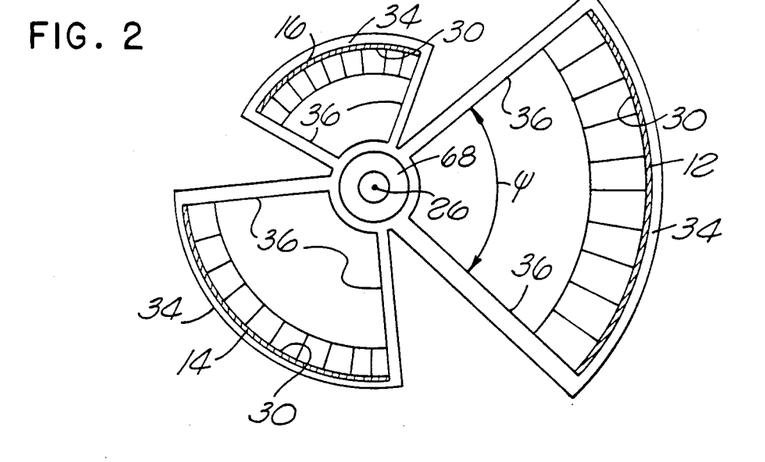
FIG. 2 is a horizontal sectional view taken along the line 2—2 of FIG. 1, including a crystal locating means omitted from FIG. 1.

Referring to FIGS. 1 and 2, a microanalysis system constructed according to a preferred embodiment of the present invention is generally designated 10. The system 10 comprises a plurality of parfocal diffracting crystal structures 12, 14 and 16 (FIG. 2) for selectively monochromatizing and focusing X-rays between common source and image points 18 and 20, respectively. The crystal structures, although typically mosaics of several crystal segments or "lamella", will be referred to herein simply as "crystals".

Focused X-rays diffracted by the crystals impinge upon a specimen 22 at the image point 20, producing fluorescence X-rays for analysis by a detector 24. The three crystals are mounted for rotation about an axis 26 between respective operative positions. In the embodiment shown, the axis of rotation 26 coincides with a line joining the source and image points.

Each of the crystals 12 through 16 is doubly curved to satisfy Bragg's Law with respect to radiation emanating over an appropriate solid angle from the source point 18. The crystals are toroidal in shape and employ Johannson-type diffraction in all planes containing the axis 26. The crystal 12, for example, monochromatizes and focuses X-radiation emanating from the source point 18 at angles of $\theta_B \pm \Delta\theta$ with respect to the source-to-image axis 26 (see FIG. 3C), in each plane which contains the source and image points and falls within a preselected angle $\psi$ about the source to image axis (see FIG. 3B).

Figure 3A:
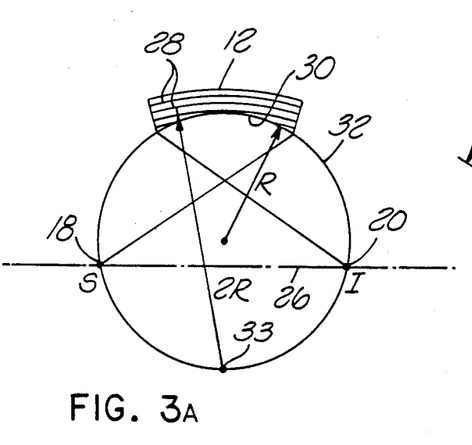
FIG. 3A is a schematic representation of the operative environment surrounding a single diffraction crystal of the present invention, taken in a plane containing the source and image points of the system and illustrating the crystal thickness in exaggerated form.
Figure 3B:
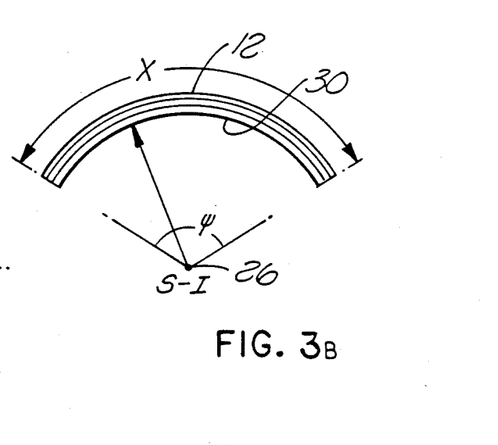
FIG. 3B is a schematic view of the cross section of the crystal illustrated in FIG. 3A, along a plane perpendicular to that of FIG. 3A.
Figure 3C:
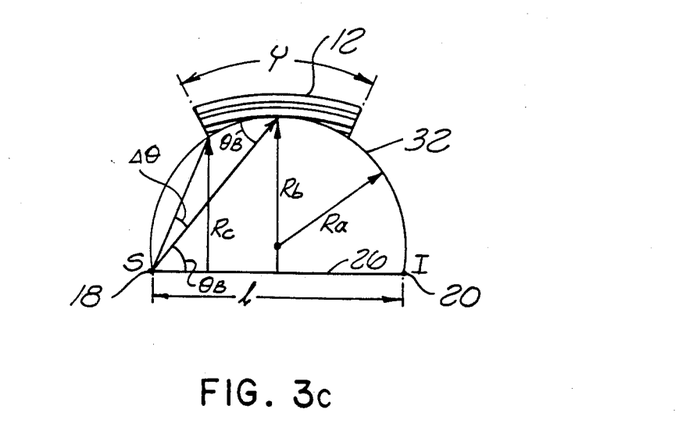
FIG. 3C is a schematic representation similar to FIG. 3A, showing various dimensions and angles.

Referring to the crystal 12 in more detail, FIGS. 3A and 3C illustrate the desired Johannson geometry within one of the planes containing the source and image points. In these FIGURES, the thickness of the crystal is magnified and its atomic planes 28 are shown schematically. A concave surface 30 of the crystal coincides with a Rowland circle 32 which contains the source and image points and has a radius "R". The atomic planes 28 are curved to a radius of 2R about a point 33 located opposite to the crystal on the Rowland circle.

According to known principles of diffraction, X-rays emanating from the source 18 are "reflected" from adjacent atomic planes of the crystal structure. In the plane of FIG. 3C and within an angular range ($\theta_B \pm \Delta\theta$) from the source-to-image axis, X-rays reflected by adjacent atomic planes constructively interfere at a preselected wavelength determined by the lattice parameters of the crystal material ($d_{hkl}$), the radius of the Rowland circle (R) and the working distance between the source and image points (l). The resulting radiation is highly monochromatic and is focused by the crystal at the image point 20. These diffraction principles are described in *Electron Probe Microanalysis*, Second Edition, pp. 45–47, L. S. Birks, Wiley-Interscience, 1971, which is hereby incorporated by reference.

The crystal structure 12 is curved in a direction perpendicular to the Rowland circle 32, to a configuration defined by rotation of the crystal surface and atomic planes about the source-to-image axis 26. The resulting structure is toroidal in shape and has radii of curvature varying between the values of $R_b$ and $R_c$ within planes perpendicular to the Rowland circle. It satifies Johannson geometric conditions within all planes containing both the source and image points, enabling it to monochromatize and focus X-rays emanating from the source 18 within a solid angle defined by "$\theta \pm \Delta\theta$" in the plane of a Rowland circle and "$\psi$" in a plane normal thereto. Radiation is focused to a point at the image location 20, enabling the system to detect trace amounts of impurities on a tightly localized basis.

The diffracting crystals 14 and 16 are similar to the structure 12, but with different diffraction characteristics. They embody Johannson geometry in each plane containing the source and image points, based on Rowland circle parameters different from those of the structure 12. The crystals 14 and 16 can also be made of materials different from the crystal structure 12. Because the crystals are dimensioned and oriented relative to the same source and image points, they are "parfocal" in much the same manner as different objective lenses of a microscope. That is, they are able to monochromatize and focus radiation of different predefined wavelengths between the common points.

As will be appreciated by those skilled in the art, the relationship between the source-to-image distance (l), the radius of the Rowland circle ($R_a$) and the Bragg angle ($\theta_B$), for a diffracting crystal in the Johannson focusing condition, is given by the expression:

$$l = 4R_a \cos\theta_B \sin\theta_B, \text{ with } \sin\theta_B = \frac{\lambda}{2d_{hkl}}.$$

The Bragg angle for each diffractor is, of course, determined by the crystal lattice spacing and the wavelength of desired radiation, and the source-to-image distances must be equal for the crystals to be parfocal. With these constraints, suitable Rowland circle radii for each parfocal case can be calculated from the above expression. Examples of such calculated values are given in Table I.

Referring now to FIG. 2, the diffracting crystals 12 through 16 are mounted for movement between respective operative positions relative to the source and image points. In the embodiment disclosed, the crystals are mounted for rotation together about the source-to-image axis and their concave diffracting surfaces 30 are directed toward the axis 26; however, in some cases it may be desirable to mount the crystals for rotation independently or together about an axis spaced from the source-to-image axis, for practical reasons. When three diffracting crystals are used, each preferably extends approximately 120 degrees about the axis of revolution ($\psi = 120°$ in FIGS. 2 and 3B).

As illustrated in FIG. 2, the crystals may be mounted in respective concave holders 34 which are connected for rotation about the axis 26 by a plurality of radial arms or spokes 36. When each of the crystals extends 120 degrees about the axis of revolution, the number of spokes can be reduced to three. Each spoke then supports the ends of two adjoining crystal structures. The details of the mechanism by which the crystals rotate are within the capabilities of a worker skilled in the art and have been omitted from FIG. 1 for clarity.

X-rays are produced at the source point 18 by bombardment of an anode 40 with an electron beam 42. The beam 42 is generated by a column 44 which comprises an electron gun and one or more condenser lenses (not shown) capable of producing a suitably localized beam. Each lens is of conventional design and typically includes a coil wound about a magnetic yoke to control the cross section of the electron beam. A single such lens can give suitable demagnification when the target is to be bombarded over an area between 10 and 20 microns in diameter. However, in some instances it may be desirable to reduce the beam size to approximately one micron. This can be done with additional lenses.

The anode 40 comprises a rotating disc 46 having an outer cylindrical surface 48 which defines a plurality of discrete bands 50 of target material. In the preferred embodiment, the column 44 is canted at a convenient angle, preferably approximately 30° with the vertical, and intersects the disc 46 at the source point 18. The disc rotates within a horizontal plane to prevent overheating and is movable vertically, as indicated at 52, to select the band 50 bombarded by the electron beam. Contamination of the anode can be minimized by a jet of gas directed onto the anode from a nozzle 53. This makes it possible to use inexpensive diffusion pumps for evacuating the electron beam column. In an alternative embodiment, the column can be vertical if the disc 46 is either beveled or canted to produce a suitable angle of incidence of the electron beam relative to the surface of the anode. In any case, the angle of incidence of the electron beam must be at least a preselected minimum value for satisfactory operation. Similarly, the angle of emergence of X-rays from the anode, which is not necessarily equal to the angle of incidence of electrons, must be at least a preselected value. While the minimum useful angles can be determined from known behaviors of electron beams incident on solid targets and X-ray beams emerging from solid targets, the disclosed angle of 30° is well within the acceptable range.

As an additional constraint on the geometry of the system 10, the system is preferably arranged so that the surface of the sample or specimen 22 is horizontal. This permits analysis of liquid samples, and eliminates any tendency of samples to slide on the supporting surface.

The anode bands 50 are made of materials designed to produce X-ray spectra suitable for use with the different diffracting crystals. In the simplest arrangement, there are three bands, each producing radiation of a wavelength which is constructively reinforced by one of crystals in a first order diffracting process. Alternatively, one or more of the bands can be made of a material generating X-rays suitable for second order diffraction from one of the crystals in the geometric configuration of FIG. 1, or a combination of materials giving rise to multiple characteristic X-ray lines. The materials of the bands 50 can also be placed in close proximity to each other so that the electron beam activates two of the materials at one time.

A plurality of filters 54 may be provided, if desired, to attenuate bremsstrahlung produced at the source point 18 relative to the characteristic X-rays desired for diffraction. The filters can be thin films of the target materials, based on the principle that a material works as a natural filter for X-rays produced by bombardment of the same material with an electron beam. Such a filter, which may be approximately 0.5 mils (12.5 microns) thick, preferentially passes the characteristic X-rays of the material.

In the embodiment of FIG. 1, the detector 24 and the sample 22 are located in air while the crystals 12 and 14 are located within a vacuum chamber 56. The vacuum chamber is provided with a lower wall 58 having a window 60 for passage of X-rays out of the vacuum chamber in the operative positions of the crystal structures. The window 60 may be a suitable X-ray transmissive window of conventional design, enabling the specimen and detector to be maintained in an environment different from the electron beam column. This is possible because, unlike electron beams, X-rays can pass through suitable window materials. Alternatively, a window could be located between the X-ray source and the crystals in order to provide a suitable non-absorbing path for the X-rays, e.g., helium or a differing degree of vacuum.

The detector 24 may be any suitably sensitive device for detecting X-rays, such as an energy dispersive spectrometer (EDS) or a wavelength dispersive spectrometer (WDS). The EDS detector may be a solid state device, specifically one of lithium-drifted silicon operated at cryogenic temperatures. It collects all wavelengths of X-rays at once and sorts them out with a multichannel analyzer which measures the height of detector output pulses. The pulse height is proportional to the energy of X-ray photons. Such detectors have high collection efficiencies and are very compact. Therefore, it is possible to place them very close to the sample and to analyze a large solid angle of radiation. However, EDS detectors can produce overlapping spectral lines with complex samples because the "L" lines of one element may overlap the "K" lines of another. Resolution of the spectral lines suffers as a result.

Wavelength dispersive spectometers, on the other hand, have higher spectral resolution and poorer efficiency than energy dispersive spectrometers. They are also slower, in that they must scan the applicable wavelength range. However, in doing so they can handle more counts at each wavelength. Typically, a WDS system will have three or four diffracting crystals or separate spectrometers.

The system 10 of FIG. 1 has an optical viewing capability for monitoring alignment of the X-ray beam with a sample. The sample is mounted to an X-Y table 62, and illuminated in the same manner as in a metallurgical microscope so it may be viewed by an operator through an objective lens 64 and a mirror 66. Thus, the operator can locate the point of impact of the X-rays relative to a reticule in the microscope eye piece. Remote control of the X-Y table 62 permits correction or alteration of the fluorescence excitation location. In addition, a baffle 68 may be provided along the source-to-image axis 26 to prevent X-rays from traveling directly to the sample from the source point 18.

Table I is a compilation of typical geometric parameters for the diffracting crystals 12 through 16.

TABLE I

TYPICAL GEOMETRIC PARAMETERS FOR DIFFRACTORS

| Crystal | Plane of Refl. | $2d_{hkl}$ | $\lambda$ | $\theta_B$ | $R_a$ | $R_b$ | $R_c$ | x · y | Collection Efficiency* $\frac{1}{4}\pi$ · (solid angle) |
|---|---|---|---|---|---|---|---|---|---|
| LiF | 200 | 4.028 | 1.54 | 22.47° | 2.78" | .828" | .778" | 1.73" × 1.94" | .022 |
| LiF | 400 | 2.014 | 1.54 | 49.87° | 1.99" | 2.33" | 2.21" | 4.87 × 1.34 | .044 |
| LiF | 440 | 1.424 | 0.71 | 29.90° | 2.27" | 1.13" | .93" | 2.36 × 1.58 | .029 |
| NaCl | 400 | 2.88 | 1.54 | 32.32° | 2.17" | 1.24" | 1.11" | 2.59 × 1.51 | .031 |
| NaCl | 440 | 2.036 | 1.54 | 49.15° | 1.99" | 2.27" | 2.15" | 4.74 × 1.39 | .044 |

$R_a$ = Radius of Rowland circle (in.)
$R_b$ = Maximum radius of curvature about axis of symmetry
$R_c$ = Minimum radius of curvature about axis of symmetry
x · y = blank size in inches
*Collection efficiency for 100% reflection and 120° sector assuming $\theta = \theta_B \pm 10°$ The parameters relate to crystals of LiF and NaCl, and contemplate "reflection" from specific planes of atoms. In addition, the listed parameters assume that the source-to-image dimension (l) is 3.93 inches (10 cm.), that the source-to-image axis is perpendicular to the specimen, and that the electron beam impinges on the anode at an angle of 30° relative to the surface thereof. The lattice parameters ($2d_{hkl}$), the Bragg angle ($\theta_B$), and the wavelength of radiation constructively reinforced at that angle, are given for each crystal material and reflective plane. The dimensional parameters illustrated in FIGS. 3A, 3B and 3C are also given, as are calculated collection efficiencies obtainable with such diffracting crystals. As seen from Table I, the Bragg angle in the preferred embodiment of the invention is between approximately 22 and 50 degrees. This range is limited by geometric constraints imposed by incorporation into a practical instrument, but does not represent an absolute limit on useful angles.

Of additional interest is Table II, which indicates the approximate intensities of output signals in alternative systems using EDS and WDS detectors. In each case, the intensity (I) is given by the following expression:

$$I = \frac{I_b}{1.6 \times 10^{-19}} \cdot E_1 \cdot E_2 \cdot E_3 \cdot E_4$$

wherein $I_b$ is the current of the electron beam in amperes, $E_1$ is the number of X-ray photons produced at the anode for each electron, $E_2$ is the diffractor efficiency as a function of the angle subtended by the diffractor about the source-to-image axis, $E_3$ is the efficiency of X-ray fluorescence excitation at the sample, and $E_4$ is the efficiency of X-ray detection.

TABLE II

| CALCULATED INTENSITIES | | |
|---|---|---|
| | Fixed Target, EDS | Rot. Target, WDS |
| $I_b$ = target current (amperes) | $.05 \times 10^{-3}$ | $1 \times 10^{-3}$ |
| $E_1 = \frac{\text{x-ray photons}}{\text{electron}}$ | $10^{-4}$ | $10^{-4}$ |
| $E_2$ = diffractor eff. ($\phi = 120°$) | $7 \times 10^{-3}$ | $7 \times 10^{-3}$ |
| $E_3$ = x-ray excit. eff. | $10^{-2}$ | $10^{-2}$ |
| $E_4$ = x-ray det. eff. | $1.5 \times 10^{-2}$ | $5 \times 10^{-4}$ |
| I (counting rate) | 32,000 | 21,875 |

Assuming the parameters of Table II, the intensity of the detected signal (I) is approximately 32,000 electrons per second for an EDS system using a stationary target X-ray source, and approximately 21,875 electrons per second for a WDS system with a rotating target X-ray source. The figure of 32,000 counts per second exceeds the maximum counting rate detectable by an EDS system, while rates of 21,875 can be handled easily by WDS systems.

Although the parameters of the electron beam 42 can be varied considerably, the beam produced by a tungsten electron source may have a current of approximately 0.5 milliamperes at a voltage of 30 KV, in a spot having a diameter of 10 microns. The current then increases in proportion to $d^{8/3} \times V$, where "d" is the diameter of the electron beam and V is the accelerating voltage. However, in many cases cathodes of $LaB_6$ are preferred in the context of the present invention to promote longer cathode life or higher currents.

Figure 4:
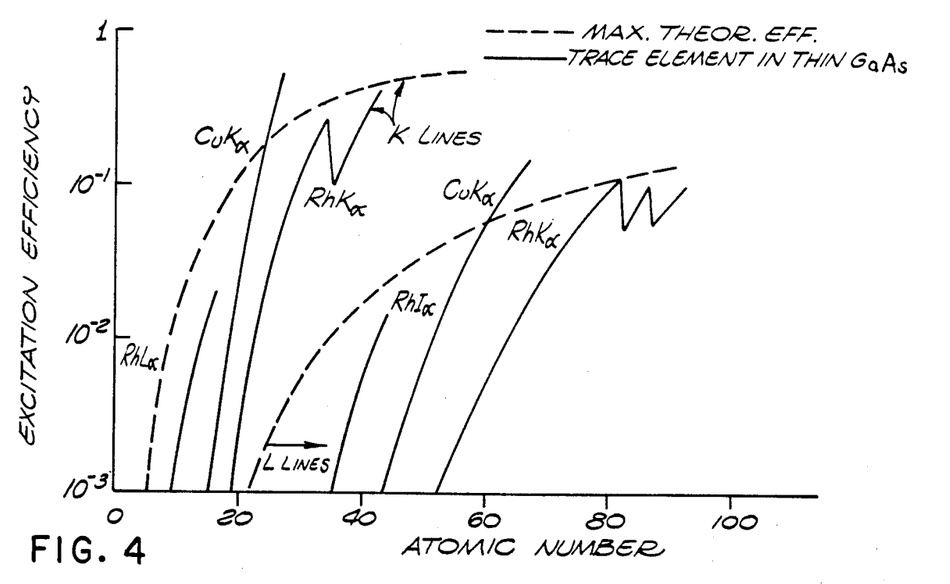
FIG. 4 is an example of published calculations as to excitation efficiencies achievable with selected wavelengths of radiation over the range of the periodic table.

FIG. 4 illustrates how X-rays representing the K and L lines of rhodium (RhK$\alpha$ and RhL$\alpha$) and the K line of copper (CuK$\alpha$) can be used to detect any element of the periodic table between atomic number 11 and atomic number 100. Therefore, three wavelengths of radiation are required to approach the theoretical excitation efficiencies shown in the dashed lines of FIG. 4. FIG. 4 relates to results calculated for the detection of trace elements in gallium arsenide (GaAs). While this figure is for the anode materials of copper and rhodium, other materials useful in the context of the present invention are molybdenum, aluminum, chromium, etc.

With regard to the diffracting crystals 12 through 16, it is believed that the alkali halides, such as NaCl and LiF, are most useful. This is because the diffracting qualities and rock salt structure of these compounds are well understood, and the materials can be handled rather easily in manufacture. Other materials of particular interest are rubidium acid thallate (RAP) and ammonium dihydrogen phosphate (ADP). Of somewhat lesser interest are ethylenediamine d-tartrate (EDT) and silicon dioxide (quartz). RAP and ADP are of interest due to their large lattice parameters.

Although alkali halides are generally considered rather brittle, they can become very ductile under appropriate temperature and surface treatment conditions. These phenomena are described in the following technical publications, the indicated portions of which are hereby incorporated by reference: Gilman, "Plastic Anisotropy of LiF and Other Rocksalt-Type Crystals", Acta Met., 7, 608–613 (1959); and Stokes et al, "Environmental Effects on the Mechanical Properties of Ionic Solids with Particular Reference to the Joffe Effect," Trans. of the Met. Soc. of AIME, 218, 655–662 (1960).

The surface treatment most useful in the present context makes use of the "Joffe Effect", whereby rocksalt-type crystals such as the alkali halides become much more ductile when placed in a solvent medium. Thus, the crystals can be placed in a solvent both during or just prior to deformation. They remain ductile after leaving the solvent bath if the surface to be placed in tension is free of microcracks and if residual solvent solution is not allowed to dry and leave a deposit on the surface.

Materials of the rocksalt and other crystal families are also more easily deformed in the plastic range at elevated temperatures because such temperatures activate a number of slip systems within the crystal lattice. With more slip systems available, a greater total strain can be achieved before fracture. This temperature dependence is discussed in Gilman, supra, Acta Met., 7, 608–613 (1959), which has been incorporated herein by reference.

Although it may be possible in some instances to produce one piece toroidal diffracting crystals having the properties described herein, the disclosed crystal structures are more easily fabricated as a number of smaller segments to limit the plastic strain required. Given the parameters of a specific material, the segments or "lamella" may be made small enough so that the strain of each segment is not sufficient to cause a fracture. The seams between segments are not a major problem, as long as the surfaces and atomic planes are properly configured. Thus, a crystal segment can be used even if it fractures during fabrication.

Figure 5A:
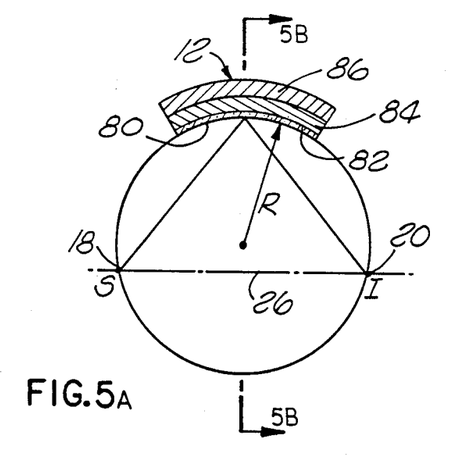
FIG. 5A is a somewhat diagrammatic cross-sectional representation of a diffraction crystal constructed according to the present invention, taken along a plane containing the source and image points.
Figure 5B:
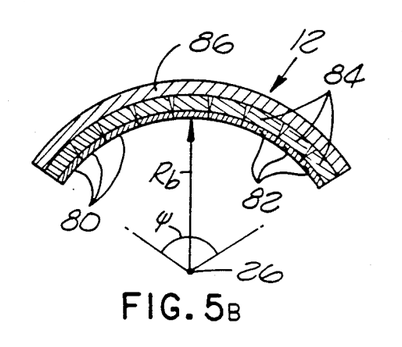
FIG. 5B is a somewhat diagrammatic cross-sectional representation taken along the line 5B—5B of FIG. 5A.
Figure 5C:
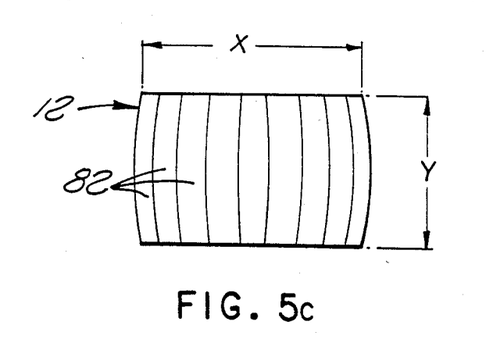
FIG. 5C is a view from the underside of the crystal of FIGS. 5A and 5B, showing the mosaic of individual lamella used to form the structure.

The preferred segmented construction is illustrated diagrammatically in FIGS. 5A, 5B and 5C, in the context of the diffracting crystal 12 and the Rowland circle 32. The surface 30 of the crystal structure is formed by lower surfaces 80 of a plurality of crystal segments 82, and the atomic planes of the crystal are similarly defined by the atomic planes of the crystal segments Each segment is curved longitudinally to a radius R, as shown in FIG. 5A, and extends a short distance in the direction perpendicular to FIG. 5A. Thus, the lateral extent of each segment is some fraction of the dimension X of FIG. 5C, and the longitudinal extent is approximately the full dimension Y. In addition, the lateral width of each segment may be reduced at each end to accommodate the unique torroidal curvature of the invention.

Each crystal segment may be mounted to an individual mounting die 84 for handling and retention of shape. The mounting dies and crystal segments are then applied to a concave holder 86 in a final assembled condition. The lower surfaces 80 of the crystal segments then define the desired crystal surface 30, and the atomic planes of the segments are aligned in the Johannson geometry. The assembled crystal structure is mountable in the system 10 through the holder 86.

Figure 6:
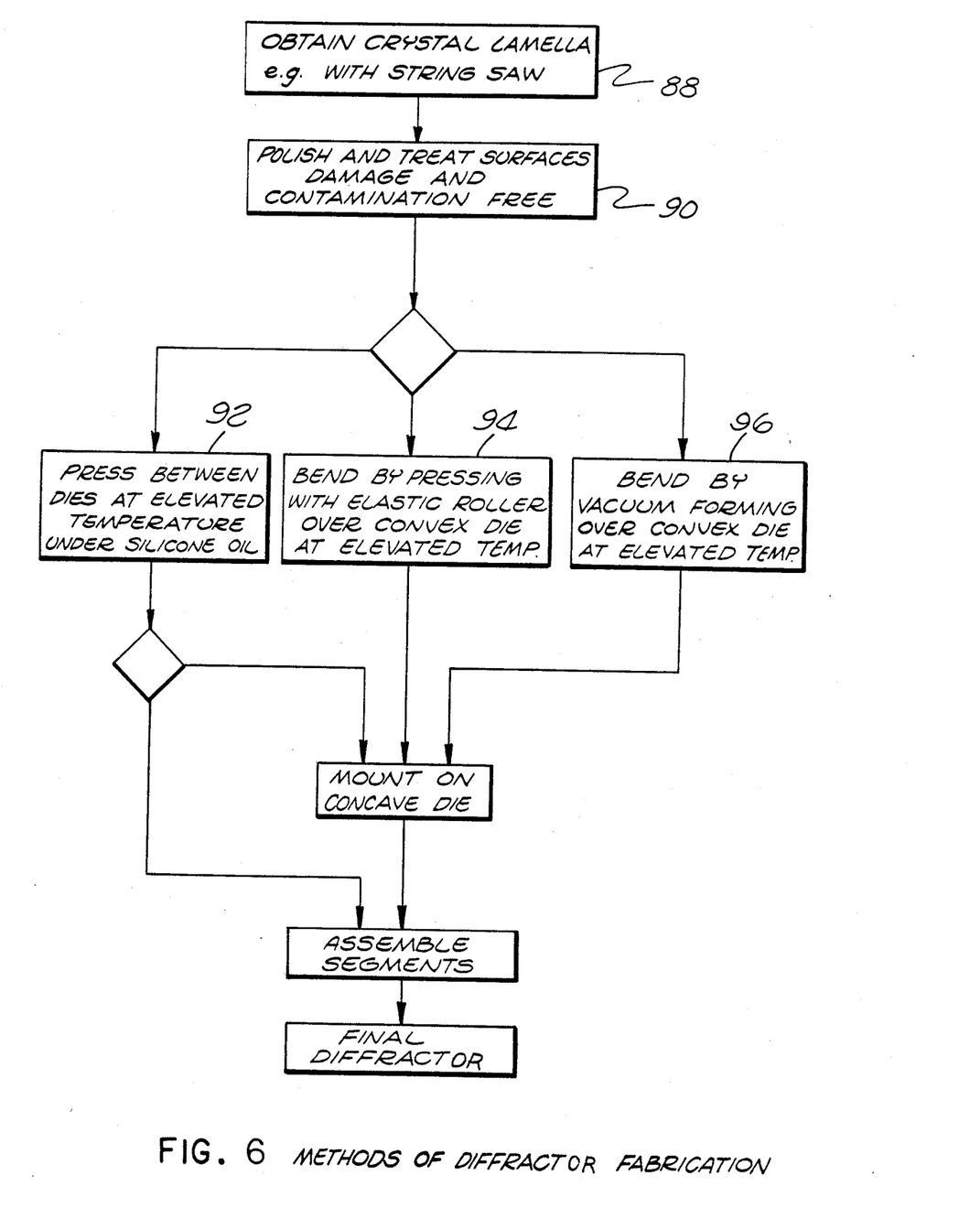
FIG. 6 is a flow chart illustrating various steps and alternative steps in the process of fabricating a diffracting crystal structure according to the present invention.

The preferred method of fabricating the diffracting crystals 12 through 16 is outlined in FIG. 6. The first step, designated 88, is to obtain suitable crystal lamella for use as the crystal segments 82. The lamella are preferably cut from a single crystal of the desired material with a string saw. The atomic planes of the crystal being cut are preferably flat, and each lamella is cut to a radius equal to twice that of the Rowland circle for which it is intended. Alternatively, a flat crystal segment can be ground to the appropriate radius, although this process is time consuming and wasteful of material.

Figure 7A:
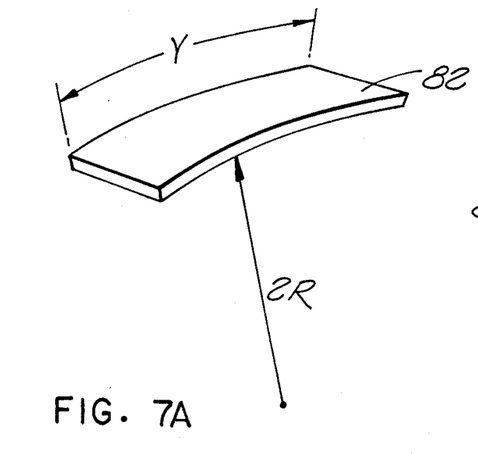
FIG. 7A is a perspective representation of one of the lamella used to form the crystal structure, prior to being formed to a desired overall curvature.

The configuration of the lamella after cutting is shown in FIG. 7A. As mentioned above, the dimensions of the lamella are small enough that the desired toroidal curvature can be achieved without exceeding the fracture limit of the material. In the case of surface treated LiF or NaCl, the lamella are typically between $\frac{1}{4}$ and $\frac{1}{2}$ inch in lateral width, and approximately 2 inches long. The thickness of the lamella will vary according to the radius to which it is to be bent, and preferably is no greater than $(4 \times 10^{-3})R$, where R is the radius of the Rowland circle. Thus, the lamella should be thinner in cases of smaller radii of curvature so that they can be more easily deformed. In the case of a Rowland circle radius between approximately 2 and 3 inches, the thickness of the lamella will be between approximately 8 and 12 mils.

The next step, designated 90, is to polish and treat the surfaces of the lamella so that they are damage- and contamination-free. This is particularly important for the surface to be placed in tension when the lamella are plastically deformed. Cracks and surface imperfections are eliminated by polishing, and the surfaces are treated by soaking in a solvent or suitable etchant to trigger the Joffe effect. The crystal should then be bathed in a suitable drying liquid to remove the solvent or etchant and prevent its evaporation in the crystal surface. In the case of NaCl, suitable solvent and drying liquids would be water and alcohol, respectively. During this process, it is also desirable to avoid exposing the crystal to ozone.

Figure 7B:
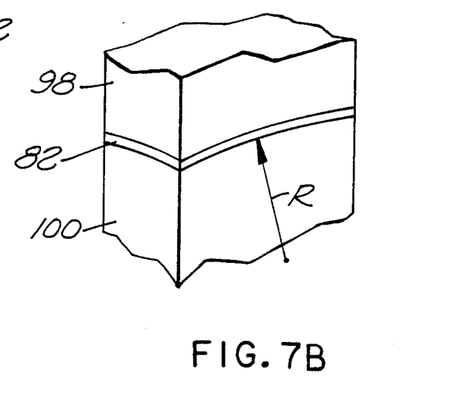
FIG. 7B is a schematic representation in perspective showing one of the lamella being shaped between a pair of dies.

After the crystal surface has been treated and dried, the crystal is deformed according to one of three processes, designated 92, 94 and 96, respectively. The step 92, illustrated schematically in FIG. 7B, involves pressing each segment 82 between upper and lower dies 98 and 100, preferably under silicone oil. The two dies conform to the desired toroidal configuration of the finished crystal, having a radius of R in the plane of the eventual Rowland circle, and radii between $R_b$ and $R_c$ in the lesser direction perpendicular to the Rowland circle. The upper die 98 is typically concave while the lower die 100 is convex, and the lower die may be made of a silicone rubber to avoid damaging the crystal's surface.

Figures 7C, 7D:
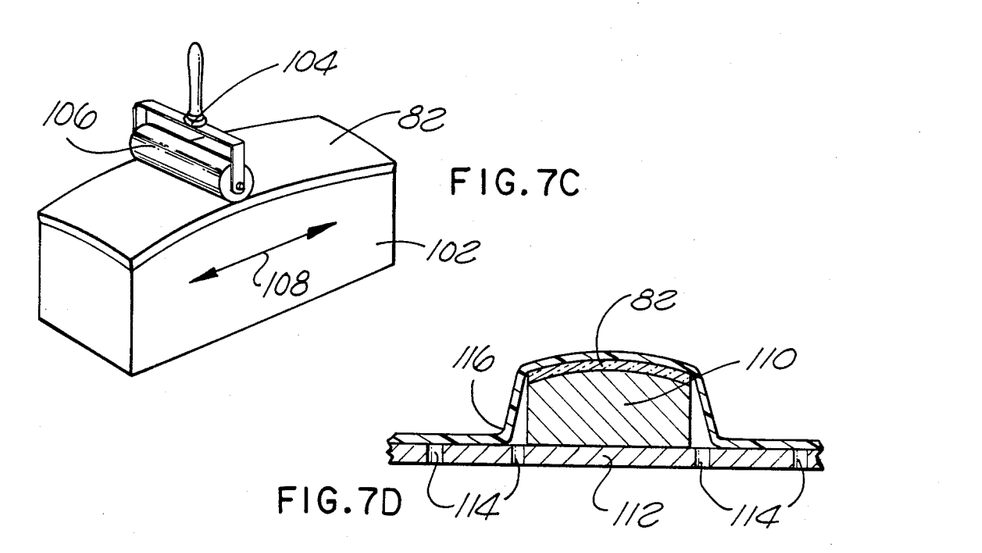
FIG. 7C is a schematic representation in perspective of one of the lamella being shaped by rolling against a die.
FIG. 7D is a vertical cross-sectional view of one of the lamella being shaped by vacuum forming techniques.

The alternative step 94, illustrated schematically in FIG. 7C, involves bending the segment 82 by pressing it downwardly over a lower convex die 102 using a forming roller 104. The roller has a rolling element 106 of suitable elastomeric material to yieldingly urge the fragile crystal segment against the die. The process is preferably carried out at elevated temperature, as with the other forming processes, to activate appropriate slip systems of the crystal. During the process, the roller 104 is passed back and forth over the crystal segment in the direction indicated at 108. A process of this type for fabricating cylindrically curved crystals is discussed in greater detail in Birks, *X-Ray Spectrochemical Analysis*, Appendix 2, pp. 127-131, Interscience Publishers, Inc., New York (1959), which is hereby incorporated by reference.

A further alternative deformation step 96 is illustrated in FIG. 7D. At present, this is the preferred method of crystal fabrication In the step 96, the crystal segment 82 is bent by a vacuum forming process over a convex lower die 110 at elevated temperature The die 110 is positioned on a base plate 112 having a plurality of air holes 114 for evacuation of the space around the die. When a sheet or mold 116 of elastomeric material is positioned above the crystal segment and the die, evacuation through the holes 114 causes the sheet or mold to be forced downwardly by ambient air pressure against the crystal segment. The segment is forced smoothly against the die until it conforms to the desired configuration. The sheet 116 can be made of any flexible material, such as buterate or silicone rubber, which is impermeable to air and possesses the tensile strength required to draw the crystal segment against the die. The attractiveness of this method lies primarily in the fact that the crystal is never contacted on its critical tensile side by a die or other rigid element applying a localized force. Rather, the force is distributed over the area of the crystal segment, minimizing the chance of breakage during the forming process.

Figure 7E:
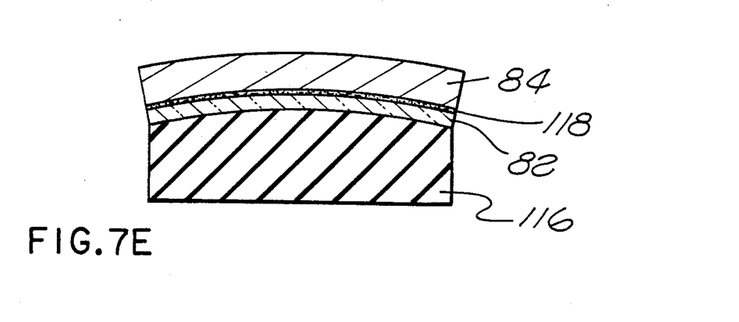
FIG. 7E is a vertical cross-sectional view of one of the lamella being mounted to a concave die following the shaping operation.

After the crystal segments are formed by the steps 92, 94 or 96, they are preferably mounted on concave mounting dies 84 of the type described in connection with FIG. 5A and 5B. This process is illustrated in FIG. 7E, wherein a crystal segment is engaged at the concave surface thereof by a convex die 116 which is preferably made of an elastomeric material, such as silicone rubber, or coated with such a material to avoid scratching of the crystal segment. The segment is retained in position against the mounting die by a suitable adhesive 118. The segments 82 and the mounting dies 84 are then mounted as a unit within the concave holder 86, illustrated in FIG. 5A, and attached to the rotatable mounting frame 36 (FIG. 1) of the system 10. Alternatively, the crystal segments can be assembled in the holder 86 without the individual mounting dies 84. This arrangement is more compact, but requires more care and sophistication in the assembly process.

The fabrication process described above is designed to produce the necessary double curvature of the crystal material without disrupting the ability of the material to diffract x-radiation. In this process, it is desirable to produce a network of edge dislocations of the crystal lattice, rather than deforming the lattice in a series of "slip bands". After fabrication, the surface and atomic planes of the plastically deformed crystals can be investigated by X-ray topography, using a microfocus X-ray source of the type embodied in the system 10.

The spatial resolution of a focused image obtained with the plastically deformed crystals of the invention depends upon the half-width of the rocking curve for the crystal, and upon the primary and secondary extinction coefficients of the material. Therefore, it may be desirable to resort to polygonalization of the crystal to fine tune its efficiency, either up or down. Polygonalization is an increase in the size of mosaic blocks within a crystal lattice, and is caused by suitable heat treatment. It may increases the primary extinction coefficient in one dimension by causing a coarsening of the structure near the surface. The effect is a trade-off, enhancing efficiency in some regions and reducing it in others. It is desirable to obtain an optimum size of mosaic blocks to maximize the integrated reflection coefficient and the primary extinction coefficient of the crystal, as described in *The Crystalline State*, Volume II "The Optical Principles of the Diffraction of X-Rays", pp. 267–305, R. W. James, G. Bell & Sons, Ltd., 1958, which is hereby incorporated by reference. Heat treatment for polygonalization would take the form of annealing at an elevated temperature. Execution of this step is well within the capabilities of one skilled in the art of crystal fabrication.

The rocking curve half-width, defined as the rate of drop-off in intensity of a diffracted beam as the angle of incidence varies from the Bragg angle, is increased by imperfections in the surface and atomic planes of a crystal. An increase in the rocking curve width can have a beneficial effect on the efficiency of the crystal, but causes a poorer signal-to-background ratio and poorer accuracy of focus. It is a trade-off in efficiency, similar to polygonalization. The rocking curve half-width can be increased by surface treatment, if desired. Specifically, such treatment can take the form of controlled grinding or abrading of the surface.

Spatial resolution of the focused image can be enhanced further by use of thin sections of sample or specimen material. This minimizes problems due to spread of the focused beam as it passes through the sample, possible inhomogeneity of the sample, and increased absorption of X-rays coming out of the sample from greater depths. However, the trade-off here is that the output signal obtained by the system is somewhat reduced. The thickness of the sample section must therefore be chosen to be at least great enough to provide a usable output signal. Typically, sample sections as commonly used in optical microscopy by transmitted light may be used, for example, on the order of 10 microns thick for biological specimens and semiconductors or 30 microns thick for geological specimens.

In operation, a sample 22 may be analyzed by the microanalysis system 10 of FIG. 1 by sequentially exposing the specimen to monochromatic radiation from each of the three diffracting crystal structures, 12 through 16. One or more bands of target material on the surface of the anode 40 are thus irradiated by the electron beam 42 for monochromatization and focusing by each of the diffracting crystals. The irradiated location of the sample 22 is monitored through the mirror 66 and the lens 64, and is controlled by the X-Y table 62. Fluorescence radiation produced at the image point 20 is detected and analyzed by the device 24 to determine the presence and concentrations of various constituent and trace elements. The use in the present invention of a highly focused beam of X-rays which have been monochromatized to a very high degree permits accurate results to be obtained from areas of the sample approximately 10 to 20 microns in diameter, and possibly from areas as small as 1 micron in diameter. The concentrations of materials detectable by the system 10 is believed to range as low as 1 part per million.

While certain specific embodiments of the present invention have been disclosed as typical, the invention is of course not limited to these particular forms, but rather is applicable broadly to all such variations as fall within the scope of the appended claims. As an example, the parfocal toroidal diffracting crystals of the present invention are useful for a wide variety of monochrometers and spectrometers, apart from the microanalysis system 10. The system 10 is merely one of the most critical and demanding uses known to the applicant for such highly focusing crystals. Similarly, numerous variations of the components of the system 10, including the arrangement and number of the diffracting crystals relative to the source and image locations, can be made without deviating from the scope of the invention.

What is claimed is:

1. A selectable X-ray monochromator comprising:
   means for generating X-rays emanating from a preselected source location;
   a plurality of diffracting crystal means selectively actuable to respective stationary operative positions relative to said source location and a preselected image location;
   each diffracting means comprising toroidal crystal means which, in the operative position of the diffracting means, satisfies Johannson geometric conditions within a plurality of planes containing the source and image locations to substantially monochromatize X-rays emanating from the source location and focus said X-rays onto a sample at the image location; and
   the diffracting means having different preselected diffracting properties and being parfocal with each other relative to the source and image locations.

2. The monochromator of claim 1 wherein:
   each diffracting means comprises toroidal crystal means having a plurality of substantially parallel atomic planes adjacent to a primary crystal surface, the crystal surface coinciding with a plurality of Rowland circles of preselected radius which contain the source and image locations in the operative position of the diffracting means, and the atomic planes being curved in the plane of each Rowland circle to twice the preselected radius about a point on the circle diametrically opposed from the primary crystal surface.

3. The monochromator of claim 2 which further comrises:
   an anode containing a plurality of preselected target materials; and
   means for selectively bombarding said target materials with an electron beam to generate X-rays of preselected spectra at the source location 4. The monochromator of claim 1 wherein:
   the diffracting crystal means are rotatable together about a preselected axis for movement between said respective operative positions 5. The monochromator of claim 4 wherein:
   each diffracting means defines a concave diffracting surface portion facing inwardly toward the preselected axis.

6. The monochromator of claim 4 wherein:

the preselected axis passes through said source and image locations.

7. Apparatus for X-ray microanalysis comprising:

means for generating X-rays emanating from a preselected source location over a preselected solid angle;

a plurality of diffracting crystal means selectively actuable to respective stationary operative positions relative to the source location and a preselected image location;

each diffracting means comprising toroidal crystal means which, in the operative position of the diffracting means, satisfies Johannson geometric conditions within a plurality of planes containing the source and image locations to substantially monochromatize X-rays emanating from the source location and focus the X-rays onto a sample at the image location;

the diffracting means having different preselected diffracting properties and being parfocal with each other relative to the source and image locations; and means for detecting and analyzing fluorescence X-rays emitted by the sample.

8. The apparatus of claim 7 wherein:

each of the diffracting means comprises toroidal crystal means having a plurality of substantially parallel atomic planes adjacent to a primary crystal surface, the crystal surface coinciding with a plurality of Rowland circles of preselected radius which contain the source and image locations in the operative position of the diffracting means, and the atomic planes are curved in the plane of each Rowland circle to a radius of twice the preselected radius about a point on the circle diametrically opposed from the primary crystal surface.

9. The apparatus of claim 8 wherein the X-ray generating means comprises:

an anode containing a plurality of preselected target materials; and means for selectively bombarding the target materials with an electron beam to generate X-rays of preselected spectra at the source location 10. The apparatus of claim 9 wherein:

the anode comprises a rotating surface portion having individual bands of said target materials thereon; and the rotating portion is movable between a plurality of conditions to selectively expose the bands to the electron beam and generate X-rays of different energy spectra.

11. The apparatus of claim 10 wherein:

the bands of target material are spaced axially along the rotating means; and the rotating means is movable axially between said plurality of conditions.

12. The apparatus of claim 10 which further comprises:

a plurality of filters associated with respective bands of the rotating means for minimizing bremsstrahlung produced by the bands;

each filter containing the material of the band with which it is used.

13. The apparatus of claim 8 wherein:

the diffracting crystal means are mounted for rotation together about a preselected axis for movement between said respective positions 14. The apparatus of claim 13 wherein:

the primary crystal surface of each diffracting means faces inwardly toward the preselected axis.

15. The apparatus of claim 13 wherein:

the preselected axis passes through the source and image locations.

16. The apparatus of claim 8 which further comprises:

means for viewing the sample during X-ray fluorescence analysis; and means for adjusting the location on the sample at which X-ray fluorescence occurs.

17. The apparatus of claim 16 wherein:

the viewing means comprises means for reflecting visible light associated with fluorescence of the sample to a remote viewing location.

18. The apparatus of claim 17 wherein:

the means for adjusting the location of fluorescence comprises X-Y table means.

* * * * *